(12) United States Patent
Hoen et al.

(10) Patent No.: US 11,262,797 B1
(45) Date of Patent: Mar. 1, 2022

(54) COMPUTER SYSTEMS WITH WEARABLE FORCE SENSING DEVICES

(71) Applicant: Apple Inc., Cupertino, CA (US)

(72) Inventors: Storrs T. Hoen, Brisbane, CA (US); Kathryn P. Crews, Menlo Park, CA (US); J. Stephen Smith, San Jose, CA (US)

(73) Assignee: Apple Inc., Cupertino, CA (US)

( * ) Notice: Subject to any disclaimer, the term of this patent is extended or adjusted under 35 U.S.C. 154(b) by 159 days.

(21) Appl. No.: 16/678,976

(22) Filed: Nov. 8, 2019

Related U.S. Application Data

(60) Provisional application No. 62/793,292, filed on Jan. 16, 2019.

(51) Int. Cl.
| | | |
|---|---|---|
| *G06F 1/16* | (2006.01) | |
| *A61B 5/00* | (2006.01) | |
| *A61B 5/11* | (2006.01) | |
| *G02B 27/01* | (2006.01) | |
| *A61B 5/024* | (2006.01) | |
| *G06F 3/01* | (2006.01) | |

(52) U.S. Cl.
CPC .......... *G06F 1/163* (2013.01); *A61B 5/02438* (2013.01); *A61B 5/1118* (2013.01); *A61B 5/681* (2013.01); *G02B 27/017* (2013.01); *G06F 3/011* (2013.01); *A61B 2562/0219* (2013.01)

(58) Field of Classification Search
CPC ....... G06F 1/163; G06F 3/011; G02B 27/017; A61B 5/02438; A61B 5/1118; A61B 5/681; A61B 2562/0219
See application file for complete search history.

(56) References Cited

U.S. PATENT DOCUMENTS

| | | | |
|---|---|---|---|
| 6,486,872 B2 | 11/2002 | Rosenberg et al. | |
| 7,106,313 B2 | 9/2006 | Schena et al. | |
| 7,202,851 B2 | 4/2007 | Cunningham et al. | |
| 7,253,803 B2 | 8/2007 | Schena et al. | |
| 8,947,383 B2* | 2/2015 | Ciesla | G06F 3/044 345/173 |
| 10,013,062 B1* | 7/2018 | Corson | G06F 3/016 |
| 10,310,608 B1* | 6/2019 | Keller | G06F 3/014 |
| 10,353,466 B1* | 7/2019 | Keller | G06F 3/011 |
| 11,009,949 B1* | 5/2021 | Elias | G06F 3/044 |

(Continued)

*Primary Examiner* — Amare Mengistu
*Assistant Examiner* — Jennifer L Zubajlo
(74) *Attorney, Agent, or Firm* — Treyz Law Group, P.C.; G. Victor Treyz; David K. Cole

(57) ABSTRACT

A system may include a wearable electronic device that gathers force input. The device may transmit force measurement information and other input to external equipment such as a head-mounted device. The wearable electronic device may have a force sensor that gathers force measurements as the wearable electronic device is being worn. The force sensor may have a force sensor housing structure configured to form a fluid-filled channel and one or more collapsible force sensor elements such as collapsible fluid-filled domes or other protruding portions of the force sensor housing structure. A pressure sensor may monitor changes in pressure in a fluid that fills the channel and the fluid-filled domes. The monitored changes in pressure represent force measurements for force applied by a user's body part or other objects on the collapsible force sensor elements.

24 Claims, 12 Drawing Sheets

(56) References Cited

U.S. PATENT DOCUMENTS

| | | | |
|---|---|---|---|
| 2003/0117371 A1* | 6/2003 | Roberts | G06F 3/014 345/156 |
| 2004/0174337 A1* | 9/2004 | Kubota | G06F 3/016 345/156 |
| 2008/0226134 A1* | 9/2008 | Stetten | G06F 3/016 382/114 |
| 2012/0182135 A1* | 7/2012 | Kusuura | G06F 3/014 340/407.1 |
| 2014/0104142 A1* | 4/2014 | Bickerstaff | G02B 27/017 345/8 |
| 2016/0103544 A1 | 4/2016 | Filiz et al. | |
| 2016/0202755 A1 | 7/2016 | Connor | |
| 2016/0278665 A1* | 9/2016 | Ferreira | A61B 5/0053 |
| 2016/0338644 A1* | 11/2016 | Connor | A61B 5/11 |
| 2017/0300115 A1* | 10/2017 | Kerr | G06F 3/011 |
| 2018/0107277 A1* | 4/2018 | Keller | G06F 3/016 |
| 2018/0179051 A1* | 6/2018 | Keller | F16K 99/0049 |
| 2018/0209562 A1* | 7/2018 | Keller | F16K 99/0061 |
| 2018/0303383 A1* | 10/2018 | Connor | G06F 3/011 |
| 2018/0356893 A1* | 12/2018 | Soni | G06F 3/0346 |
| 2019/0113972 A1* | 4/2019 | Hoen | D03D 1/0088 |
| 2019/0201785 A1* | 7/2019 | Heubel | G06F 3/016 |
| 2019/0310706 A1* | 10/2019 | Wang | H02J 7/32 |
| 2019/0354179 A1* | 11/2019 | Hoen | A41D 1/005 |
| 2020/0174583 A1* | 6/2020 | Wang | G06F 3/011 |
| 2021/0027360 A1* | 1/2021 | Shmueli | G06Q 30/0635 |
| 2021/0081048 A1* | 3/2021 | Sedal | G06T 19/006 |

* cited by examiner

US 11,262,797 B1

COMPUTER SYSTEMS WITH WEARABLE FORCE SENSING DEVICES

This application claims the benefit of provisional patent application No. 62/793,292, filed Jan. 16, 2019, which is hereby incorporated by reference herein in its entirety.

FIELD

This relates generally to electronic systems, and, more particularly, to systems with electronic devices such as wearable electronic devices.

BACKGROUND

Electronic devices such as computers can be controlled using computer mice and other input accessories. Cellular telephones and computers may have touch sensitive input surfaces that gather user input. In computer-generated-reality systems, input accessories such as force-feedback gloves can be used to control virtual objects.

Devices such as these may not be convenient for a user, may be cumbersome or uncomfortable, or may not satisfactorily gather input or provide output.

SUMMARY

A system may include a wearable electronic device that gathers force input. The device may transmit force measurement information and other input to external equipment such as a head-mounted device to control the external equipment. For example, the device may have wireless communications circuitry that wirelessly transmits force measurement information to an external electronic device to control the external device.

The wearable electronic device may have a force sensor that gathers force measurements from a body part of a user as the wearable electronic device is being worn against the body part of the user. The force sensor may have a force sensor housing structure that is coupled to a wearable electronic device housing structure. The wearable electronic device housing structure may be configured to be worn on a finger, hand, arm, foot, leg, head, wrist, or other body part of a user.

The force sensor may be used to make measurements of forces applied to the force sensor by the user as the body part of the user or other external object presses against the force sensor. The force sensor housing structure in the force sensor may be configured to form a fluid-filled channel and one or more collapsible force sensor elements such as collapsible fluid-filled domes or other protruding portions of the force sensor housing structure. The housing structure may be supported by the wearable electronic device housing structure so that the domes face the body part of the user and are compressed by force from the body part (e.g., force that arises as the body part presses against the force sensor as the body part moves through the air and/or as the body part contacts an external object). A pressure sensor may monitor changes in pressure in a fluid that fills the channel and the fluid-filled domes. The monitored changes in pressure represent force measurements for force applied by the user's body part or other external objects on the collapsible force sensor elements.

DETAILED DESCRIPTION

Electronic devices may be used to gather user input and to provide a user with output. For example, a wearable device may gather force input from a user's fingers or other body parts. This force input may be gathered as the wearable device is being worn on the user's body part and, if desired, as the user is touching or otherwise interacting with external objects. Gathered force input may be provided to electronic equipment with a display such as a head-mounted device and/or a computer. For example, force input may be used in moving objects that are displayed on a display in a system such as a computer-generated-reality system. Wearable devices with force sensor input may be worn on a user's fingers, hand, arm, foot, and/or other body parts. If desired, haptic output and/or other output may be supplied to the user with the wearable device.

Figure 1:
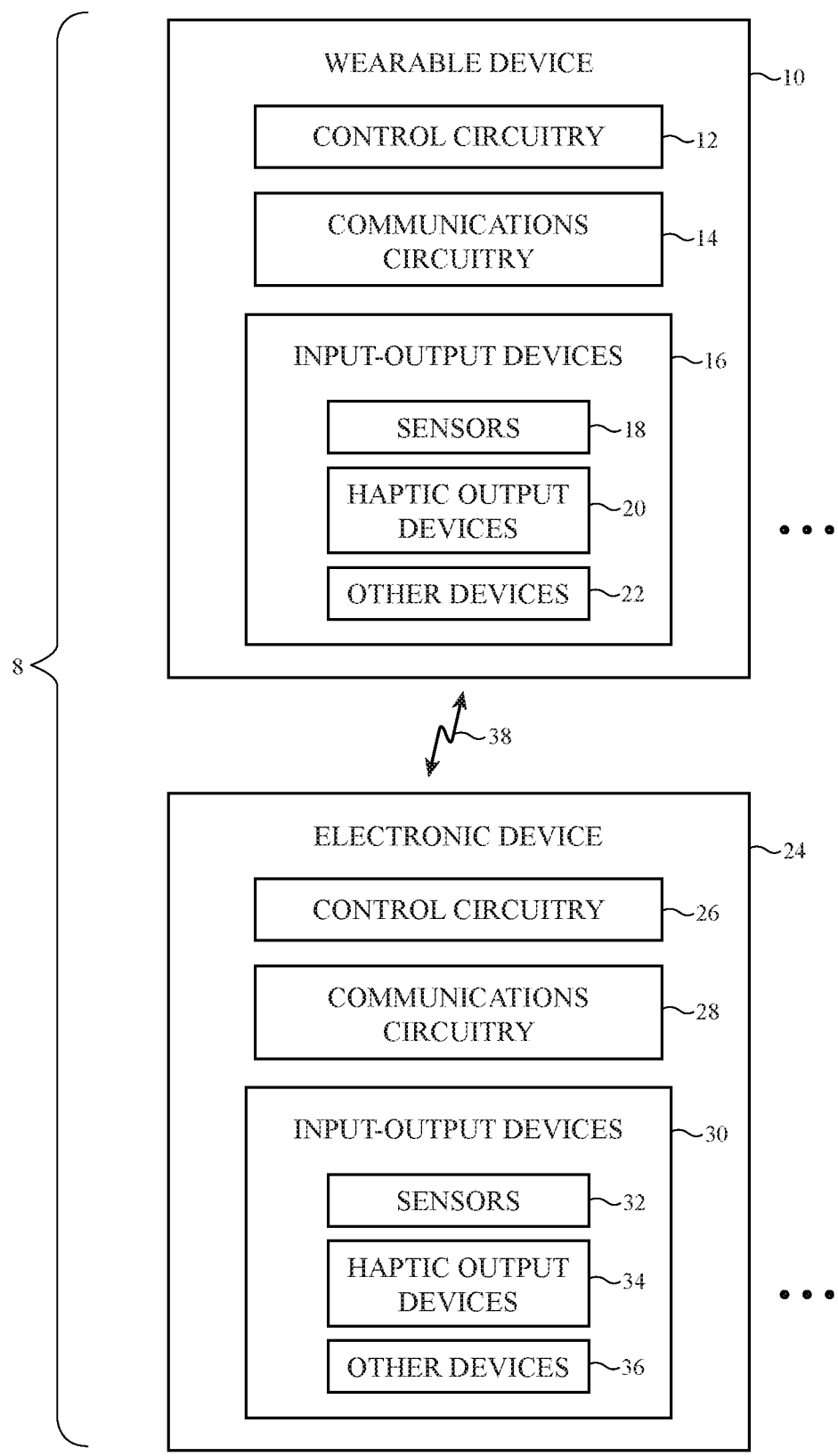
FIG. 1 is a schematic diagram of an illustrative system with electronic devices in accordance with an embodiment.

FIG. 1 is a schematic diagram of an illustrative system of the type that may include one or more wearable devices and/or other input-output devices for gathering user input by making force measurements and/or other sensor measurements. As shown in FIG. 1, system 8 may include electronic devices such as wearable device(s) 10 and other electronic device(s) 24. Each wearable device 10 may be worn by a user. Devices 10 may gather user input and may therefore sometimes be referred to as user input devices. Devices 10 may serve as output devices (e.g., by providing haptic output and other output and/or by otherwise serving as an input-output device for system 8). Additional electronic devices in system 8 such as devices 24 may, if desired, provide output to a user using one or more devices 10 and may receive user input from one or more devices 10. For example, device 10 may have wireless communications circuitry that wirelessly transmits force measurement information to one or more devices 24 for use in controlling devices 24. Devices 24 may perform operations in response to this user input (e.g., devices 24 may be controlled using the user input from wearable devices 10).

Devices 24 may include devices such as a laptop computer, a computer monitor containing an embedded computer, a tablet computer, a desktop computer (e.g., a display on a stand with an integrated computer processor and other computer circuitry), a cellular telephone, a media player, or other handheld or portable electronic device, a smaller device such as a wristwatch device, a pendant device, a headphone or earpiece device, a head-mounted device such as glasses, goggles, a helmet, or other equipment worn on a user's head, or other wearable or miniature device, a television, a computer display that does not contain an embedded computer, a gaming device, a remote control, a navigation device, an embedded system such as a system in which equipment is mounted in a kiosk, in an automobile, airplane, or other vehicle, a removable external case for electronic equipment, a strap, a wrist band or head band, a removable cover for a device, a case or bag that has straps or that has other structures to receive and carry electronic equipment and other items, a necklace or arm band, a wallet, sleeve, pocket, or other structure into which electronic equipment or other items may be inserted, part of a chair, sofa, or other seating (e.g., cushions or other seating structures), part of an item of clothing or other wearable item (e.g., a hat, belt, wrist band, headband, sock, glove, shirt, pants, etc.), a mouse, trackpad, stylus, ear buds, or other accessories, or equipment that implements the functionality of two or more of these devices. Devices 24 may, if desired, include cloud-based computing equipment (e.g., one or more computers that are accessed over the internet or other wide area network and/or over local area networks).

In some arrangements, a single device 24 (e.g., a head-mounted device) may be used with one or more wearable devices 10. In other arrangements, multiple devices 24 (e.g., a head-mounted device and an associated host computer or a head-mounted device, host computer, and online computer) may be used in system 8 with one or more wearable devices 10. In yet other configurations, system 8 includes only one or more wearable devices 10 (e.g., a device worn on a user's hand, head, arm, leg, foot, wrist, finger, palm, ankle, elbow, torso, or other body part). In some arrangements, device may have a wearable device housing such as an external shell structure or other housing member that is flexible, but that creates resistance when bent by a user's fingers or other body part. In this type of arrangement, force measurements with a force sensor inside the flexible member or other housing structure of the device may be used as user input as a user is wearing device 10 in the air without contacting external objects. If desired, wearable device 10 may have force sensing circuitry that detects when a user who is wearing device 10 touches and presses against external objects. Input from wearable device 10 may control one or more devices 24, which may include a cellular telephone, tablet computer, laptop computer, wristwatch device, head-mounted device, a device with a speaker, and/or other electronic devices (e.g., a device with a display, audio components, and/or other output components). Configurations in which system 10 includes one or more devices 10 and one or more devices 24 may sometimes be described herein as an example.

Devices 10 and 24 may include control circuitry 12 and 26. Control circuitry 12 and 26 may include storage and processing circuitry for supporting the operation of system 8. The storage and processing circuitry may include storage such as nonvolatile memory (e.g., flash memory or other electrically-programmable-read-only memory configured to form a solid state drive), volatile memory (e.g., static or dynamic random-access-memory), etc. Processing circuitry in control circuitry 12 and 26 may be used to gather input from sensors and other input devices and may be used to control output devices. The processing circuitry may be based on one or more microprocessors, microcontrollers, digital signal processors, baseband processors and other wireless communications circuits, power management units, audio chips, application specific integrated circuits, etc.

To support communications between devices 10 and 24 and/or to support communications between equipment in system 8 and external electronic equipment, control circuitry 12 may communicate using communications circuitry 14 and/or control circuitry 26 may communicate using communications circuitry 28. Circuitry 14 and/or 28 may include antennas, radio-frequency transceiver circuitry, and other wireless communications circuitry and/or wired communications circuitry. Circuitry 14 and/or 26, which may sometimes be referred to as control circuitry and/or control and communications circuitry, may, for example, support bidirectional wireless communications between devices 10 and 24 over wireless link 38 (e.g., a wireless local area network link, a near-field communications link, or other suitable wired or wireless communications link (e.g., a Bluetooth® link, a WiFi® link, a 60 GHz link or other millimeter wave link, etc.). Devices 10 and 24 may also include power circuits for transmitting and/or receiving wired and/or wireless power and may include batteries. In configurations in which wireless power transfer is supported between devices 10 and 24, in-band wireless communications may be supported using inductive power transfer coils (as an example).

Devices 10 and 24 may include input-output devices such as devices 16 and 30. Input-output devices 16 and/or 30 may be used in gathering user input, in gathering information on the environment surrounding the user, and/or in providing a user with output. Devices 16 may include sensors 18 and devices 30 may include sensors 32. Sensors 18 and/or 32 may include force sensors (e.g., strain gauges, capacitive force sensors, resistive force sensors, force sensors that include pressure sensors that detect pressure in a fluid that is coupled to one or more force sensing elements formed from collapsible fluid-filled force sensor protrusions, etc.), audio sensors such as microphones, touch and/or proximity sensors such as capacitive sensors, optical sensors such as optical sensors that emit and detect light, ultrasonic sensors, and/or other touch sensors and/or proximity sensors, monochromatic and color ambient light sensors, image sensors, sensors for detecting position, orientation, and/or motion (e.g., accelerometers, magnetic sensors such as compass sensors, gyroscopes, and/or inertial measurement units that contain some or all of these sensors), muscle activity sensors (EMG) for detecting finger actions, radio-frequency sensors, depth sensors (e.g., three-dimensional optical sensors such as structured light sensors configured to project dots of infrared light onto three-dimensional surfaces of real-world objects and sense three-dimensional shapes by capturing images of the dots using an infrared image sensor and/or optical depth sensors based on stereo imaging devices), optical sensors such as self-mixing sensors and light detection and ranging (lidar) sensors that gather time-of-flight measurements, optical sensors such as visual odometry sensors that gather position and/or orientation information using images gathered with digital image sensors in cameras, gaze tracking sensors, visible light and/or infrared cameras having digital image sensors, humidity sensors, moisture sensors, and/or other sensors. In some arrangements, devices 10 and/or 24 may use sensors 18 and/or 32 and/or other input-output devices 16 and/or 30 to gather user input (e.g., buttons may be used to gather button press input, touch sensors overlapping displays can be used for gathering user touch screen input, touch pads may be used in gathering touch input, microphones may be used for gathering audio input, accelerometers may be used in monitoring when a finger contacts an input surface and may therefore be used to gather finger press input, etc.). If desired, device 10 and/or device 24 may include rotating buttons (e.g., a crown mechanism on a watch or finger device or other suitable rotary button that rotates and that optionally can be depressed to select items of interest). Alphanumeric keys and/or other buttons may be included in devices 16 and/or 30.

Devices 16 and/or 30 may include haptic output devices 20 and/or 34. Haptic output devices 20 and/or 34 can produce motion that is sensed by the user (e.g., through the user's fingertips). Haptic output devices 20 and/or 34 may include actuators such as electromagnetic actuators such as solenoids, motors, piezoelectric actuators, electroactive polymer actuators, vibrators, linear actuators, rotational actuators, actuators that bend bendable members, actuator devices that create and/or control repulsive and/or attractive forces between devices 10 and/or 24 (e.g., components for creating electrostatic repulsion and/or attraction such as electrodes, components for producing ultrasonic output such as ultrasonic transducers, components for producing magnetic interactions such as electromagnets for producing direct-current and/or alternating-current magnetic fields, permanent magnets, magnetic materials such as iron or ferrite, and/or other circuitry for producing repulsive and/or attractive forces between devices 10 and/or 24). In some configurations, actuators for creating forces in device 10 may be used in pressuring fluid that in turn presses against a user's finger and/or other body parts.

If desired, input-output devices 16 and/or 30 may include other devices 22 and/or 36 such as displays (e.g., in device 24 to display images for a user), status indicator lights (e.g., a light-emitting diode in device 10 and/or 24 that serves as a power indicator, and other light-based output devices), speakers and other audio output devices, electromagnets, permanent magnets, structures formed from magnetic material (e.g., iron bars or other ferromagnetic members that are attracted to magnets such as electromagnets and/or permanent magnets), batteries, etc. Devices 10 and/or 24 may also include power transmitting and/or receiving circuits configured to transmit and/or receive wired and/or wireless power signals.

Figure 3:
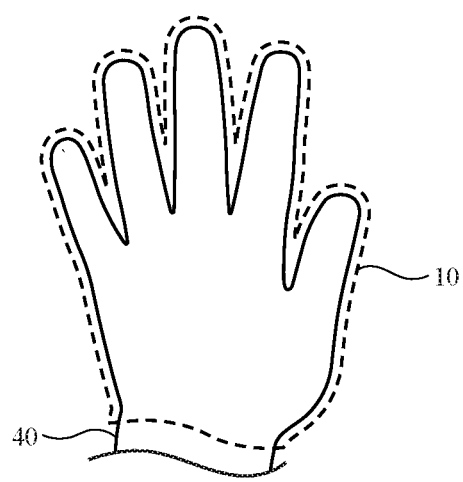
FIGS. 2, 3, 4, and 5 are views of wearable electronic devices being worn on illustrative body parts of a user in accordance with embodiments.
Figure 2:
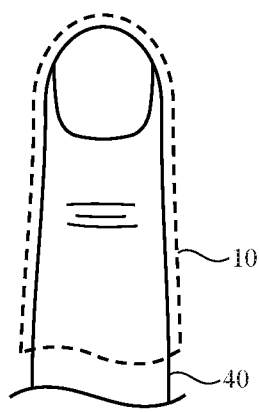
Figure 4:
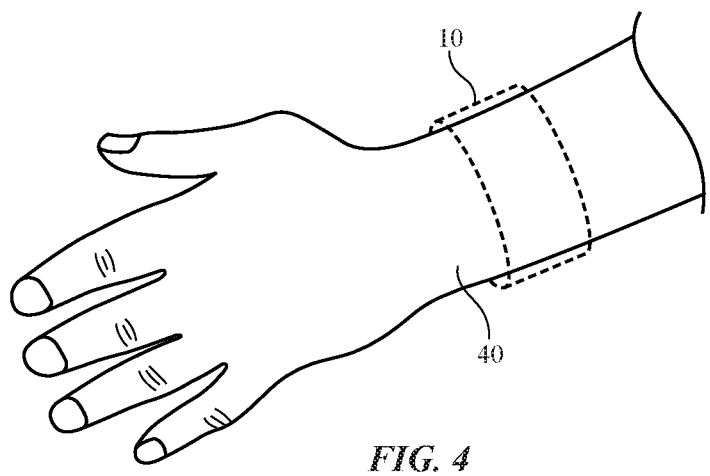
Figure 5:
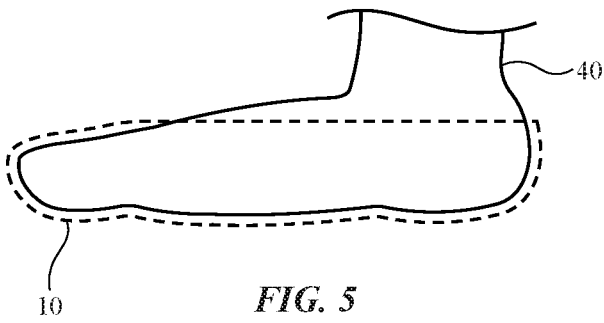

Wearable device 10 may be worn on any body part of a user (see, e.g., illustrative body parts 40 of FIGS. 2, 3, 4, and 5). As shown in FIG. 2, body part 40 may be a finger and device 10 may serve as a finger-mounted device that is worn on the tip of the finger. As shown in FIG. 3, body part 40 may be a user's hand and device 10 may be a glove, a fingerless glove, or other device that is worn over a user's palm and/or one or more fingers. As shown in FIG. 4, device 10 may be worn on a user's appendage such as a user's arm. Body part 40 may be, for example, a user's arm, leg, or other appendage and device 10 may have the shape of a circular band or cuff that is worn around the user's arm, leg, or other appendage (e.g., device 10 may form a blood pressure measuring device and/or a device that measures heart rate). As shown in FIG. 5, device 10 may be worn one or against a surface of the user's foot (e.g., body part 40 may be a foot). Device 10 may, for example, cover the sole and/or side surfaces of the user's foot. Device 10 of FIG. 5 may be a shoe, sock, foot pad, or other item that is worn on the user's foot. Body part motions, body part pressure against housing structures in device 10 and/or against external objects, and/or other user activity can be measured as the user's body part moves and device 10 moves. If desired, arrangements in which device 10 is worn against user body parts other than the body parts of FIGS. 2, 3, 4, and 5 may be used. The configurations of FIGS. 2, 3, 4, and 5 are illustrative.

Figure 6:
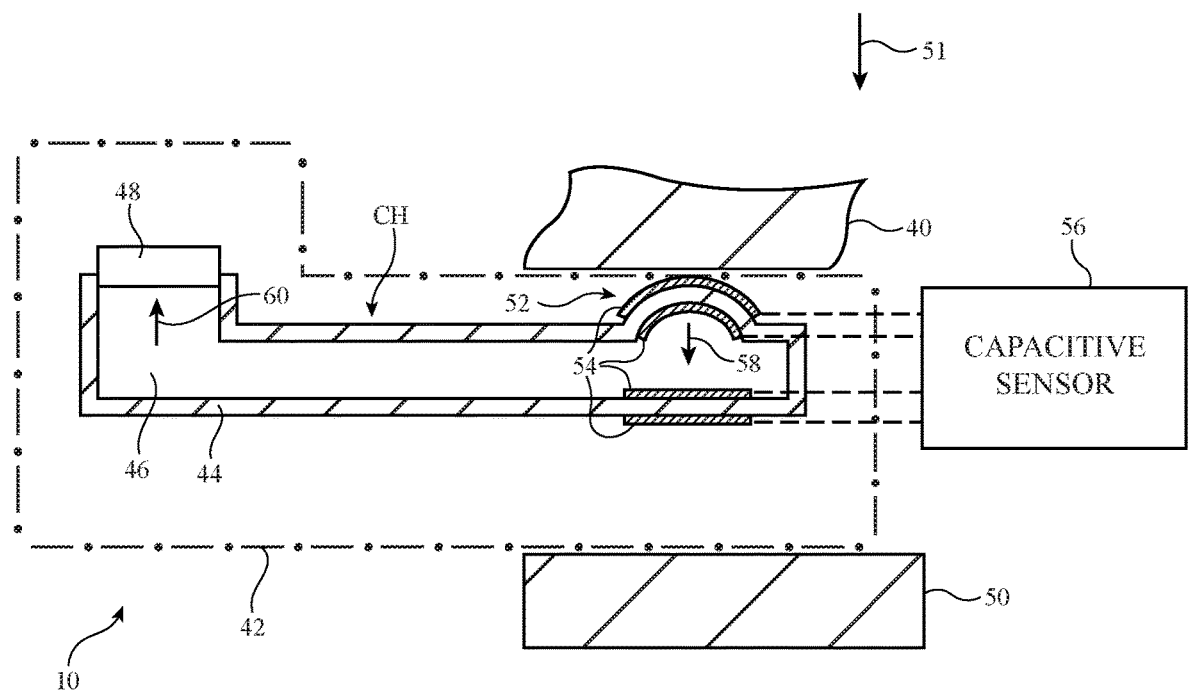
FIG. 6 is a side view of an illustrative wearable electronic device with a force sensor in accordance with an embodiment.

FIG. 6 is a diagram of device 10 showing how device 10 may have force sensing circuitry. In the example of FIG. 6, device 10 includes a force sensor that has a pressure sensor such as pressure sensor 48 that is coupled by fluid 46 to a force sensor element such as a collapsible force sensor element at a different location than sensor 48. The force sensor element of FIG. 6 is formed from collapsible fluid-filled force sensor protrusion such as dome 52. Dome 52 may form a hemispherical protrusion that collapses fully or partially in direction 58 due to pressure between dome 52 and the user's body 40 or other external object. For example, device 10 may be compressed between body 40 and object 50 when body part 40 moves in direction 51. Object 50 may be an external object or a housing structure in wearable device 10 (e.g., a housing member that covers at least the rear face of the force sensor while the front face of the force sensor with dome 52 faces the user's body part). If desired, collapsible fluid-filled force sensor protrusions may have other shapes such as half-cylinder shapes (e.g., elongated ridges having a semi-circular cross-sectional shape on one side and a flat shape on an opposing side), other elongated ridge-shaped protrusions, or protrusions with other shapes.

Fluid 46 may be a gas such as air, nitrogen, argon, or other gaseous substance or may be a liquid such as water, oil, a non-flammable fluorocarbon liquid that does not conduct electricity, a gel such as silicone gel, or other suitable fluid that may be pressurized by compression of dome 52. Force sensor housing 44 forms a cavity that is filled with fluid 46. This cavity may include fluid-filled channel CH and is in communication with dome 52 and pressure sensor 48. The walls of housing 44 may be configured so that channel CH has a circular cross-sectional shape, a half-cylinder shape, or other shape in which any plane normal to fluid-filled channel CH intersects the channel with an arc such as a circular arc, or other cross-sectional shape that helps channel CH resist expansion under pressure. In this way, channel CH may help convey fluid pressure changes due to compression of dome 52 to pressure sensor 48 for measurement. Fluid-filled sensing protrusions such as dome 52 can have a dome shape, a half-cylinder shape, or other fluid-filled shape in which any plane normal to the fluid-filled protrusion intersects the protrusion with an arc such as a circular arc. As an example, fluid-filled sensing protrusions can include half-cylinder portions that form semi-circular channels (e.g., channels where the cross-sectional shape includes a circular arc).

Pressure sensor 48 may be formed from an absolute or differential pressure sensor such as a microelectromechanical systems (MEMs) pressure sensor. Housing 44 may be formed from polymer, metal, glass, ceramic, and/or other materials and may include flexible and/or rigid structures. To facilitate flexibility in dome 52, portions of housing 44 such as the portion of housing 44 that forms dome 52 may be formed from flexible material such silicone, urethane, polyethylene terephthalate, nylon (polyamide), and/or other flexible polymer. When the force sensing element formed from dome 52 is compressed in direction 58, fluid 46 is pressurized within the cavity formed in force sensor housing 44. This causes fluid 46 to press against pressure sensor 48 in direction 60.

During operation of system 8, pressure sensor 48 produces output data (e.g., a pressure output signal) that is processed by processing circuitry in control circuitry 12. The output signal from pressure sensor 48 is indicative of the amount of force applied to collapsible dome 52, so this output signal serves as a measure of the amount of force detected by the force sensor formed from pressure sensor 48 and collapsible dome 52 (e.g., the output of sensor 48 serves as a force measurement output signal for the force sensor of device 10). The force sensor output signal from sensor 48 may be supplied to control circuitry 12 and, if desired, control circuitry 12 may use wireless or wired communications circuitry (e.g., circuitry 14) to transmit the force sensor measurement information from device 10 to device(s) 24 (e.g., wirelessly or via a wired link).

Force measurements may be used to control the operation of device 10 and/or device(s) 24. For example, force measurements that are gathered by device 10 and that are transmitted wirelessly or via a wired path(s) to device(s) 24 may serve as user input for controlling device(s) 24 while device(s) 24 and/or devices 10 present images, audio output, haptic output, and/or other output to a user. The user may be, as an example, interacting with a computer-generated-reality environment that is created by system 8 (e.g., device 10 may gather force input to control a computer-generated-reality system).

If desired, the force sensing circuitry of device 10 may be provided with capacitive force sensing circuitry. For example, metal traces 54 may be formed on the inner and/or outer surfaces of dome 52 and opposing portions of the walls of housing 44 to form a capacitive force sensor. Metal traces 52 may, for example, include upper and lower capacitive sensor electrodes that are coupled to capacitive sensor circuitry 56. Circuitry 56 may use the capacitive sensor electrodes to measure capacitance changes that result when the spacing between the upper and lower electrodes is varied due to deformation of dome 52.

Measurements from a capacitive force sensor circuit of the type shown in FIG. 6 may be used in place of pressure sensor measurements with pressure sensor 48 and/or may be used in addition to pressure sensor measurements made with pressure sensor 48. As an example, one or more pressure sensors 48 may be coupled to one or more corresponding rows (or columns) of one or more domes 52 using one or more corresponding fluid-filled channels CH running along a first dimension and one or more columns (or rows) of capacitive force sensor electrodes running along a second dimension that is orthogonal to the first dimension may be used in making capacitive force sensor measurements. In this way, fluid-based force sensing may be used in providing a first dimension of spatial discrimination for the force sensor of device 10 and capacitive-based force sensing may be used in providing a second dimension of spatial for the force sensor of device 10. A spatially addressable two-dimensional force sensor of this type may use both capacitive and fluid-based sensing to provide force measurements over a desired surface area of device 10. If desired, a one-dimensional force sensor or a single element force sensor may use both capacitive and fluid-based sensing. Arrangements with only capacitive sensing or only fluid-based sensing may also be used. The foregoing examples are illustrative.

The force sensor of device 10 may, if desired, be enclosed on one or more sides by an outer housing structure such as housing 42 and may be coupled to housing 42 and supported by housing 42 during operation of device 10. Polymer, metal, wood, other natural materials such as natural fibers of cotton, wool, or silk, polymer fibers such as rayon fibers, and/or other fibers, ceramic, glass, foam formed from polymer or other materials, and/or other materials (e.g., sheets of these materials, fabric formed from these materials, frame members and other members made from these materials, shell members, foam inserts located between a user's body part and other portions of device 10 and/or other structure such as a foam layer located between a user's foot and the sole of a shoe being worn by a user, etc.) may be used in forming wearable device housing 42. Housing 42 may form an exterior covering, an internal frame, and/or other support structures for device 10. If desired, force sensor housing 44 may be mounted partly or completely within a cavity formed in the interior of the housing walls that form housing 42 and may be coupled to housing 42 using adhesive or other attachment structures. In some arrangements, openings may be formed in device housing 42 (e.g., to allow domes 52 to directly contact body part 40 and/or other external objects). For example, housing 42 may have a portion that covers housing 44 and may have an opening that allows one or more domes 52 to be exposed while facing and contacting the user's body and/or domes 52 and other portions of a force sensor may be mounted in an inwardly facing configuration on an inner surface of housing 42 (as examples). If desired, a thin flexible fabric covering or other flexible layer in housing 42 may be interposed between domes 52 and the user's body.

Figure 7A:
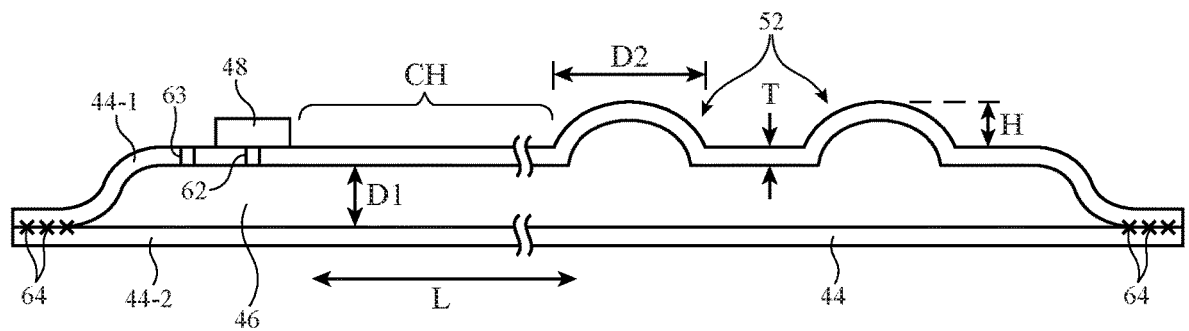
FIG. 7A is a cross-sectional side view of an illustrative force sensor in accordance with an embodiment.

A cross-sectional side view of an illustrative arrangement for forming fluid-based force sensing circuitry for device 10 is shown in FIG. 7A. As shown in FIG. 7A, force sensor housing 44 may have a first portion such as portion 44-1 that is coupled to a second portion such as portion 44-2. Portions 44-1 and 44-2 may be formed from flexible material and/or rigid material (e.g., rigid material linked by flexible hinges, etc.). By forming housing 44 at least partly using flexible materials, the force sensor of FIG. 7A may be comfortably worn close to the user's body while bending to accommodate changes in the shape of body part 40 during use of device 10.

Portion 44-1 and portion 44-2 may be different portions of a single unitary structure (e.g., a molded polymer part) or portions 44-1 and 44-2 may be separate structures (e.g., separate polymer layers) that are joined using attachment structures 64. Structures 64 may be formed from adhesive (e.g., polymer adhesive), polymer welds (e.g., joints formed from molten and/or softened parts of portions 44-1 and 44-2), and/or other attachment structures.

Fluid-filled channels such as channel CH of FIG. 6 and FIG. 7A may be characterized by a length L and diameter D1. Channel CH may have a circular cross-sectional shape (e.g., to resist expansion when fluid 46 is pressurized) and/or other suitable cross-sectional shape. The value of length L may be larger than diameter D1 (e.g., L may be at least two times D1, at least 5 times D1, at least 15 times D1, at least 40 times D1, at least 1000 times D1, less than 10,000 D1, less than 2000 D1, less than 500 times D1, etc.). The value of D1 may be at least 1 micron, at least 10 microns, at least 100 microns, at least 1 mm, at least 10 mm, less than 5 mm, less than 500 microns, less than 200 microns, less than 75 microns, less than 25 microns, or other suitable size). Channel CH may be coupled to pressure sensor 48 through an opening in portion 44-1 such as opening 62 (e.g., an opening with a size of at least 1 micron, at least 50 microns, at least 1 mm, less than 5 mm, less than 700 microns, less than 200 microns, or other suitable size). Channel CH may be coupled to one or more domes 52 (e.g., two domes in the example of FIG. 7A) and may therefore be used in supplying pressured fluid 46 to sensor 48 due to compression of any one or more of these domes 52.

Domes 52 may have a circular footprint (outline when viewed from above). The lateral dimension of domes 52 (e.g., diameter D2) may be at least 1 micron, at least 10 microns, at least 100 microns, at least 1 mm, at least 5 mm, less than 10 mm, less than 4 mm, less than 700 microns, less than 400 microns, less than 250 microns, less than 120 microns, less than 70 microns, less than 30 microns, less than 15 microns, less than 7 microns, or other suitable size. The height H of domes 52 may be less than 75% of D2, less than 70% of D2, less than 50% of D2, or less than 15% of D2 (as examples). Other dome heights may be used, if desired. Domes 52 may have a hemispherical shape or other suitable protruding shape that collapses under applied pressure and that returns to its uncollapsed shape when pressure is removed (e.g., with minimal lag). The thickness T of the walls of housing 44 may be at least 1 micron, at least 10 microns, at least 100 microns, at least 1 mm, at least 4 mm, less than 5 mm, less than 500 microns, less than 50 microns, less than 5 microns, or other suitable thickness.

In some configurations, fluid 46 may be air. To help equalize the pressure of the air in the cavity formed from force sensor housing 44 relative to ambient air pressure (e.g., the air pressure of the operating environment for device 10), housing 44 may have a pressure equalization opening such as opening 63. Opening 63 may be a through-hole opening that is unfilled with any material, may have a porous filler structure such as a fabric plug (e.g., a fabric formed from polytetrafluoroethylene or other polymer that is sufficiently porous to allow air to pass while helping to prevent ingress of moisture or other contaminants into the cavity within housing 44), and/or may have any other suitable configuration that allows air pressure to equalize between the interior of housing 44 and the exterior of housing 44 when device 10 is moved between environments of different pressures.

To prevent excessive air pressure leakage from the cavity in housing 44 that might reduce force measurement accuracy by pressure sensor 48 when dome 52 is depressed, the amount of air flow through pressure equalization openings such as opening 63 may be restricted. For example, consider an example in which ambient pressure transitions from 0.75 atm to 1 atm in time T. Opening 63 can be configured so that this 0.25 atm difference in air pressure can be accommodated within time T (e.g., so that the cavity air pressure will reach 1 atm after starting at 0.75 atm within time T), provided that time T is at least 10 s, at least 1 m, at least 1 hour, less than 2 hours, less than 0.5 hours, less than 10 m, less than 100 s, less than 5 s, or other suitable value.

Figure 7B:
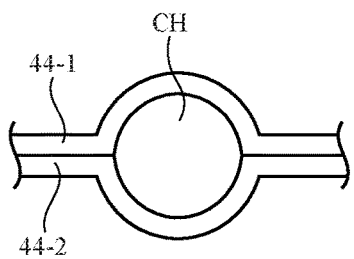
FIGS. 7B, 7C, and 7D are cross-sectional end views of illustrative force sensor structures for forming a fluid-filled cavity structure such as a fluid-filled channel in accordance with an embodiment.
Figure 7C:
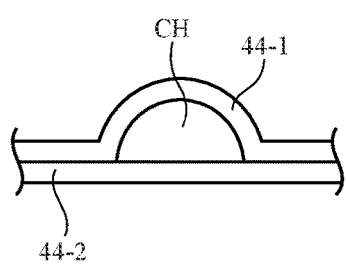
Figure 7D:
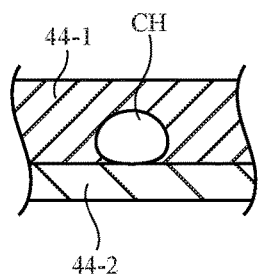

FIG. 7B shows how housing portion 44-1 and housing portion 44-2 may have protruding portions that form mating halves of channel CH. For example, channel CH may have a circular cross-sectional shape and housing portions 44-1 and 44-2 may have mating half-cylinder protrusions that form channel CH. In the example of FIG. 7C, portion 44-1 has a semicircular protrusion for forming channel CH and portion 44-2 has a planar shape. As shown in the illustrative configuration of FIG. 7D, channel CH may have a circular or nearly circular cross-sectional shape that is formed entirely or almost entirely from portion 44-1, whereas portion 44-2 may have a planar shape or other suitable shape that is used in sealing the lower edge of channel CH. Other arrangements and/or combinations of these arrangements may be used, if desired. The examples of FIGS. 7A, 7B, 7C, and 7D are merely illustrative.

Figure 8:
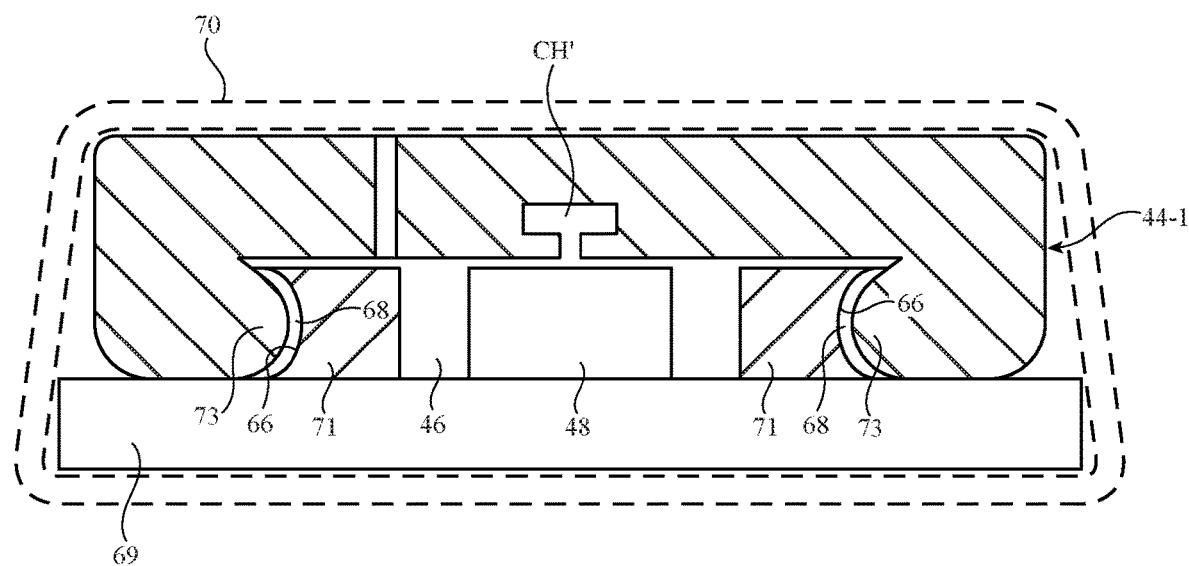
FIG. 8 is a cross-sectional side view of an illustrative force sensor having a flexible structure coupled to an attachment structure on a substrate such as a printed circuit to which a fluid pressure sensor has been mounted in accordance with an embodiment.

If desired, sensor 48 may be mounted to a substrate such as a rigid printed circuit. This type of arrangement is shown in FIG. 8. In the example of FIG. 8, pressure sensor 48 is mounted (e.g., with solder, etc.) to metal traces that form signal lines in a printed circuit such as printed circuit 69. A connector on printed circuit 69 may be used to couple the signal paths in the printed circuit to integrated circuits and other components (e.g., control circuitry 12) that are mounted on other printed circuits in device 10. Printed circuit 69 may form force sensor housing structures for the force sensor.

Flexible housing member attachment structure 71 may be attached to printed circuit 69 using adhesive, by molding attachment structure 71 to printed circuit 69, or using other attachment mechanisms. Structure 71 may be formed from molded rigid polymer or other suitable material. Force sensor housing portion 44-1 may be a flexible polymer member with a flexible protruding portion 73 that stretches over and squeezes against recessed portions of attachment structure 71 such as recessed (grooved) surface 66 of attachment structure 71, thereby holding portion 44-1 to printed circuit 69 while forming a seal for the cavity of force sensor housing 44 that retains fluid 46. If desired, sealant 68 (e.g., polymer adhesive) may be used in sealing the joint formed along surfaces 66. An optional band such as elastic band 70 may be stretched around housing portion 44-1 and printed circuit 69 to help hold portion 44-1 and printed circuit 69 together. Portion 44-1 may have a channel structure CH' that communicates with channel CH of FIG. 7A (as an example).

Figure 9:
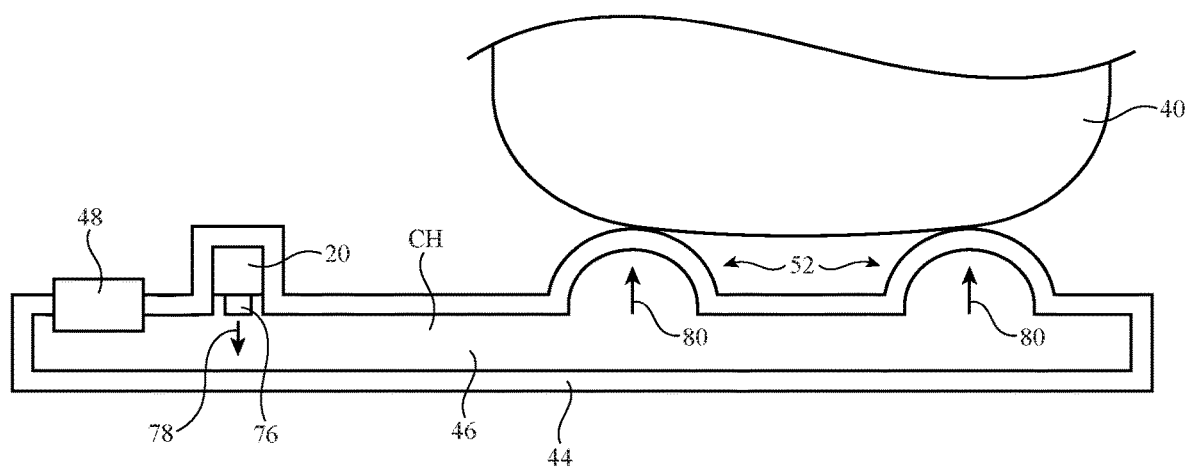
FIG. 9 is a cross-sectional side view of an illustrative force sensor device with haptic output capabilities in accordance with an embodiment.

If desired, wearable device 10 may include haptic output devices. For example, haptic output may be provided to a user with device 10 by coupling a haptic output component to force sensor housing 44 and/or other support structures in device 10 such as exterior housing 42 (FIG. 6). In the illustrative configuration of FIG. 9, haptic output is provided to body part 40 of a user by selectively pressurizing fluid 46 in channel CH, thereby forcing domes 52 outward in direction 80 against body part 40. Control circuitry 12 may, for example, direct a solenoid or other haptic component such as haptic output device 20 to extend plunger 76 momentarily into fluid 46 in direction 78, thereby creating a momentary pulse in the pressure of fluid 46 and expanding domes 52 outwardly (away from channel CH) in direction 80 toward body part 40. This approach may be used to create vibrations and/or other haptic output as domes 52 are in direct or indirect contact with body part 40. Solenoids and/or other haptic output devices that can selectively pressurize fluid 46 may also be used to create slowly varying pressure changes in fluid 46 (e.g., to tighten device 10 about a user's body or too loosen device 10 such as when housing 42 is configured to form a band or strap that surrounds body part 40). If desired, pressure measurements with pressure sensor 48 may be temporarily halted during pressurization of fluid 46 with haptic output device (component) 20 and/or measurements with pressure sensor 48 may be performed when fluid 46 is being pressurized by an electrically controlled actuator such as device 20.

Figure 10:
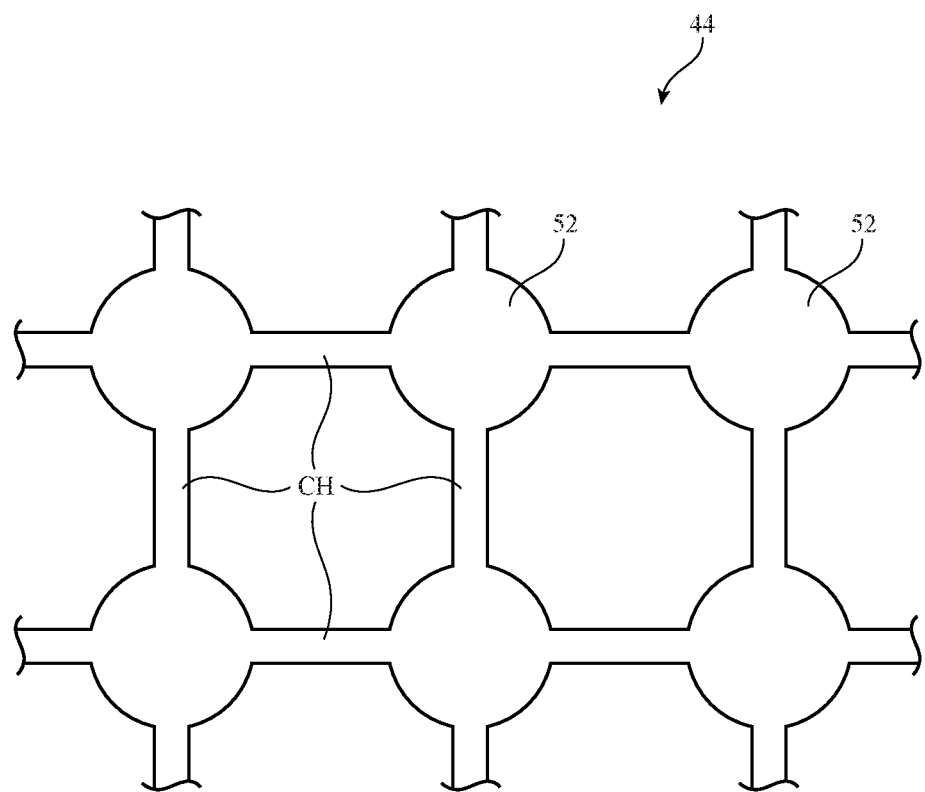
FIG. 10 is a top view of an illustrative network of collapsible fluid-filled force sensor protrusions in accordance with an embodiment.

As shown in the top view of the illustrative force sensor housing 44 of FIG. 10, force sensor housing 44 may be configured to form a network of interconnected channels CH and domes 52. By spreading out the locations of domes 52, force may be sensed over a desired enlarged surface area of device 10. Domes 52 may be arranged in one-dimensional arrays (e.g., linear sets of domes may be used), may be formed in two-dimensional arrays (e.g., rows and columns of domes 52 may cover some or all of the exposed surfaces of device 10), and/or other patterns of compressible fluid-filled force sensor protrusions may be used. The pattern of channels and domes of FIG. 10 is illustrative. Any suitable patterns for the fluid-filled cavity structures of housing 44 may be used, if desired.

Figure 11:
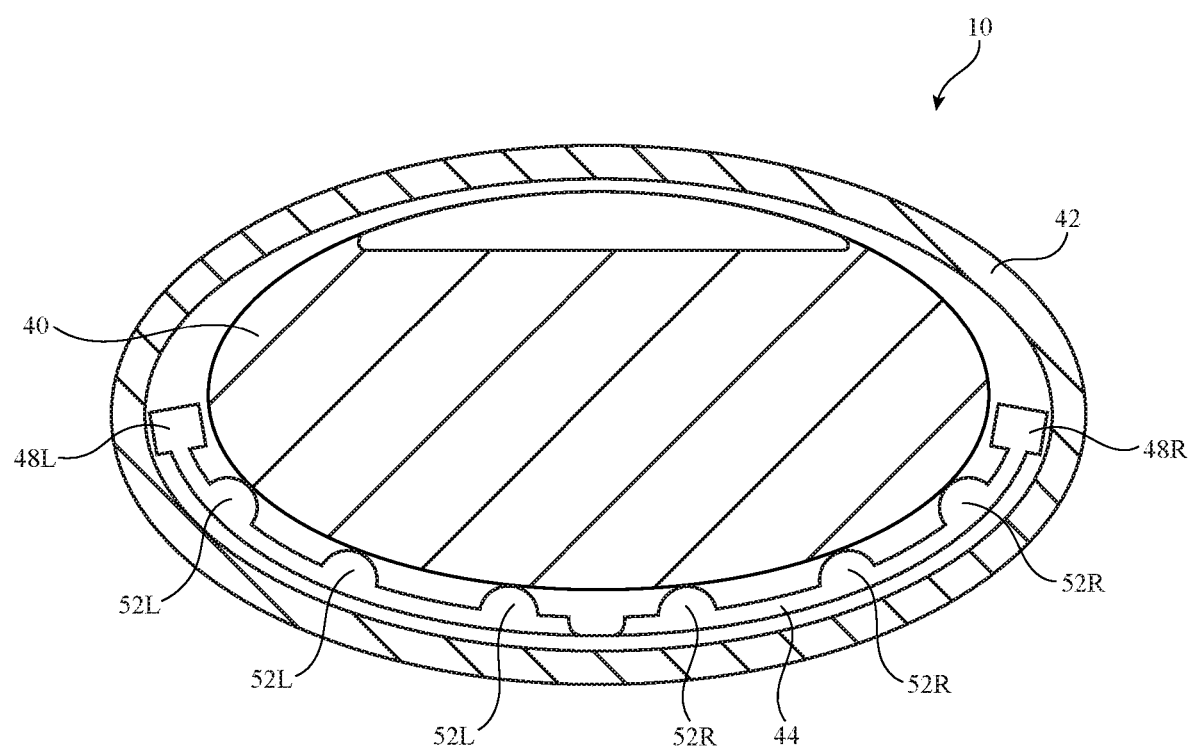
FIG. 11 is a cross-sectional end view of an illustrative wearable device on a finger of a user showing how a force sensor housing structure may be coupled to and supported by a wearable electronic device housing structure in accordance with an embodiment.

FIG. 11 is a cross-sectional end view of device 10 in an illustrative configuration in which force sensor housing 44 has a first set of fluid-filled domes 52 (domes 52L) that are coupled to a first pressure sensor 48L on the left-hand side of a user's finger (body part 40) and in which force sensor housing 44 has an independent second set of fluid-filled domes 52 (domes 52R) that are coupled to a second pressure sensor 48R on the right-hand side of the user's finger. With this type of arrangement, for example, forces can be measured when a user rolls the finger pad of the user's finger slightly to the left or right while pressing the finger against an external object (e.g., the sensor can detect the magnitudes of the forces on both sides of a user's finger and thus can measure finger rotation as the user's finger presses against a surface). External device housing 42 (e.g., a fabric layer, a polymer wall, and/or other housing structures) may be used to cover the force sensor structures formed from housing 44.

Figure 12:
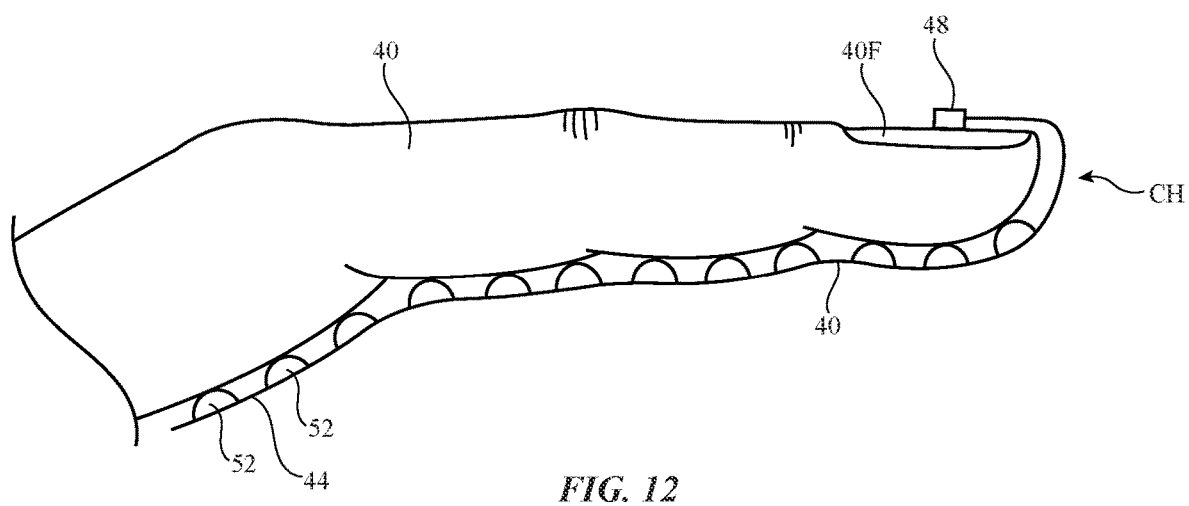
FIG. 12 is a cross-sectional side view of an illustrative force sensor oriented so that collapsible domes face a finger and palm of a user in accordance with an embodiment.

FIG. 12 is a side view of device 10 in an illustrative configuration in which body part 40 is a user's hand. As shown in FIG. 12, housing 44 may have domes 52 that cover the underside of the user's fingers and, if desired, cover the palm of the user's hand. Channel CH may be configured so that pressure sensor 48 can be located in a portion of device 10 that is not typically compressed as a user touches external objects. For example, housing structures 44 may be arranged so that pressure sensor 48 can be located above fingernail 40F on the upper surface of the user's fingertip. Device housing 42 may support housing structures 44, as described in connection with FIGS. 6 and 11.

Device housing 42 may, in general, be configured to support housing 44 and domes 52 so that domes 52 face the user's skin or other portion of body part 40 when device housing 42 is being worn by the user. For example, when device 10 is a glove or other device that is worn on a user's hand or finger, housing 42 may be configured to be worn on the user's hand or finger and housing 44 may be coupled to housing 42 in an orientation that causes domes 52 to face the skin of the user's hand or finger for direct or indirect contact with the user's hand or finger. In this way, forces created between the skin of the user's hand or finger can collapse domes 52 when device housing 42 and device 10 are pressed against external objects by the user's hand or finger. As domes 52 collapse, fluid 46 is pressurized and the increase in pressure due to the collapse of domes 52 is conveyed via fluid 46 to pressure sensor 48 so that pressure sensor 48 can produce a corresponding force sensor output signal for use by control circuitry 12 and, following wired or wireless transmission by communications circuitry 14, for use by control circuitry 26 of device 24.

If desired, device housing 42 may be configured to be worn on a user's foot (e.g., with domes 52 oriented to face the sole of the user's foot or other skin on the user's foot). The force sensor in this type of arrangement may provide circuitry in system 8 with information on the steps taken by the user, the user's running pace, and/or other foot force sensor information. Housing 42 can also be configured to be worn on a user's head (e.g., to measure head band pressure or other force between device 10 and the user's head) and/or may be worn on other body parts.

If desired, device 10 may be used to gather physiological measurements. For example, housing 42 may have a ring shape (e.g., housing 42 may form a circular band, wristwatch strap, or other housing structure with an opening that receives a user's arm, wrist, leg, ankle, finger, or other body part in which blood flows). In arrangements in which housing 42 is configured to be worn on a user's arm, wrist, leg, ankle, finger, or other body part in which blood flows, the force sensor may measure force variations on domes 52 by monitoring for corresponding fluid pressure fluctuations at pressure sensor 48 to measure blood pressure, heart rate, or other physiological attributes of the user.

Figure 13:
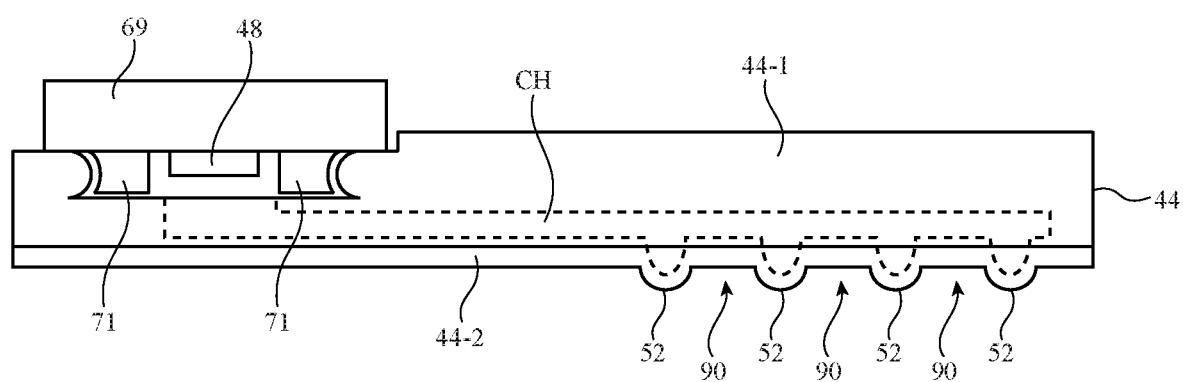
FIG. 13 is a side view of an illustrative force sensor for a wearable device showing how the force sensor housing may have locally thinned regions between respective pairs of collapsible force sensor elements in accordance with an embodiment.

In the example of FIG. 13, housing portion 44-1 has been coupled to attachment structure 71 so that pressure sensor 48, which is mounted to printed circuit 69, is coupled to the fluid-filled cavity in force sensor housing 44. As shown in FIG. 13, domes 52 have been formed in housing portion 44-2, which is coupled to housing portion 44-1 to form flexible force sensor housing 44. Locally thinned regions of housing 44 may be formed in regions 90 between respective pairs of collapsible force sensor elements such as domes 52 to facilitate bending of housing 44 during use of the force sensor to gather force sensor measurements while device 10 is being worn on a body part of a user.

Figure 14:
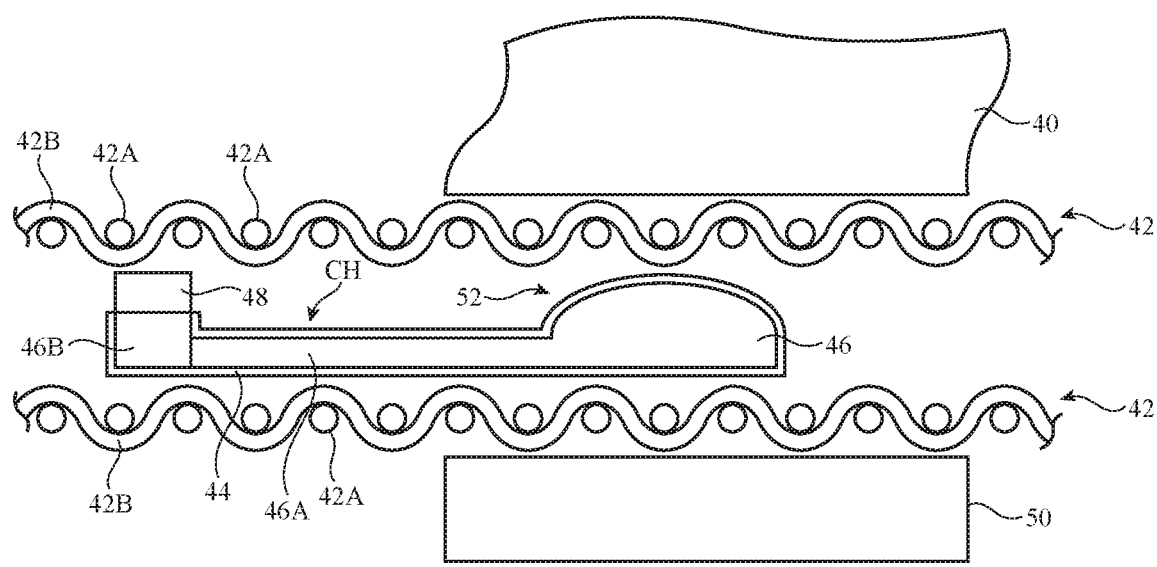
FIG. 14 is a side view of an illustrative wearable electronic device with a force sensor and a fabric housing in accordance with an embodiment.

In the example of FIG. 14, housing 42 includes fabric. The fabric may be formed from intertwined strands of material. The strands of material may be formed from polymer (e.g., rayon), metal, natural materials such as cotton, wool, silk, other materials, and/or combinations of these materials. Strand in the fabric may be intertwined by weaving, knitting, braiding, and/or other strand intertwining techniques. As shown in FIG. 14, for example, strands in the fabric of housing 42 may include woven warp strands 42A and weft strands 42B. This is illustrative. Fabric for housing 42 may include knit strands, braided strands, and/or other strands of material. Layers of polymer and/or other materials may be incorporated into housing 42 (e.g., inside and/or outside of one or more layers of fabric). There may be more than one type of fluid in the interior of the sensor. For example, fluid 46 in FIG. 14 may include first portion 46B that fills a region of channel CH that is adjacent to pressure sensor 48 and second portion 46A that fills the remainder of channel CH and protrusion 52. First portion 46B may be air or other fluid (e.g., an air bubble) and second portion 46A may be a liquid, gel, or other fluid.

Figure 15:
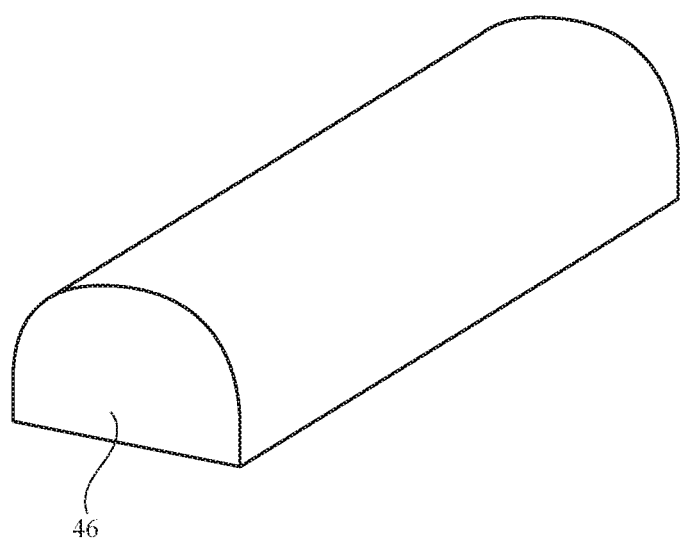
FIG. 15 is a perspective view of an illustrative half-cylinder fluid-filled structure having a semi-circular cross-sectional shape in accordance with an embodiment.

FIG. 15 is a perspective view of an illustrative half-cylinder shape that may be used in forming some or all of channel CH and/or that may be used in forming some or all of a fluid-filled protrusion (e.g., in addition to or instead of using dome 52). In general, channel CH and/or the fluid-filled protrusion(s) of device 10 may have any suitable shape such as a cross-sectional shape in which any plane that is normal to the fluid-filled structure intersects the structure with a circular arc.

As described above, one aspect of the present technology is the gathering and use of information such as sensor information. The present disclosure contemplates that in some instances, data may be gathered that includes personal information data that uniquely identifies or can be used to contact or locate a specific person. Such personal information data can include demographic data, location-based data, telephone numbers, email addresses, twitter ID's, home addresses, data or records relating to a user's health or level of fitness (e.g., vital signs measurements, medication information, exercise information), date of birth, username, password, biometric information, or any other identifying or personal information.

The present disclosure recognizes that the use of such personal information, in the present technology, can be used to the benefit of users. For example, the personal information data can be used to deliver targeted content that is of greater interest to the user. Accordingly, use of such personal information data enables users to calculated control of the delivered content. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the United States, collection of or access to certain health data may be governed by federal and/or state laws, such as the Health Insurance Portability and Accountability Act (HIPAA), whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, the present technology can be configured to allow users to select to "opt in" or "opt out" of participation in the collection of personal information data during registration for services or anytime thereafter. In another example, users can select not to provide certain types of user data. In yet another example, users can select to limit the length of time user-specific data is maintained. In addition to providing "opt in" and "opt out" options, the present disclosure contemplates providing notifications relating to the access or use of personal information. For instance, a user may be notified upon downloading an application ("app") that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of information that may include personal information data to implement one or more various disclosed embodiments, the present disclosure also contemplates that the various embodiments can also be implemented without the need for accessing personal information data. That is, the various embodiments of the present technology are not rendered inoperable due to the lack of all or a portion of such personal information data.

The foregoing is merely illustrative and various modifications can be made to the described embodiments. The foregoing embodiments may be implemented individually or in any combination.

What is claimed is:

1. A wearable electronic device, comprising:
control circuitry; and
a force sensor that supplies a force sensor output signal to the control circuitry, wherein the force sensor comprises:
   a collapsible fluid-filled force sensor protrusion having opposing first and second surfaces;
   a pressure sensor; and
   a force sensor structure that is configured to form a channel, wherein the channel is filled with fluid and is coupled between the collapsible fluid-filled force sensor protrusion and the pressure sensor, wherein the first surface of the collapsible fluid-filled force sensor protrusion faces the fluid, wherein the pressure sensor is configured to generate the force sensor output signal in response to a force on the second surface of the collapsible fluid-filled force sensor protrusion, and wherein the pressure sensor is configured to provide the force sensor output signal to the control circuitry.

2. The wearable electronic device defined in claim 1 further comprising a wearable device housing that is configured to be worn on a body part, wherein the force sensor structure comprises flexible polymer that is coupled to the wearable device housing, wherein the collapsible fluid-filled force sensor protrusion comprises a collapsible fluid-filled polymer dome, and wherein the collapsible fluid-filled polymer dome faces the body part when the wearable device housing is worn on the body part.

3. The wearable electronic device defined in claim 2 wherein the body part comprises a finger and wherein the wearable device housing is configured to be worn on the finger.

4. The wearable electronic device defined in claim 2 wherein the body part comprises a body part selected from the group consisting of: a finger, a palm, a wrist, an arm, a leg, an ankle, and a head and wherein the wearable device housing is configured to support the collapsible fluid-filled polymer dome in an orientation where the collapsible fluid-filled polymer dome faces the body part.

5. The wearable electronic device defined in claim 1 wherein the channel has a circular cross section.

6. The wearable electronic device defined in claim 1 wherein the fluid comprises air and wherein the collapsible fluid-filled force sensor protrusion comprises a hemispherical protrusion.

7. The wearable electronic device defined in claim 1 wherein the fluid comprises a liquid and wherein the collapsible fluid-filled force sensor protrusion comprises a hemispherical protrusion.

8. The wearable electronic device defined in claim 1 wherein the collapsible fluid-filled force sensor protrusion is a fluid-filled collapsible dome and wherein the force sensor structure comprises a polymer structure with multiple additional fluid-filled collapsible domes.

9. The wearable electronic device defined in claim 1 further comprising a capacitive force sensor electrode on the force sensor structure.

10. The wearable electronic device defined in claim 9 wherein the capacitive force sensor electrode overlaps the collapsible fluid-filled force sensor protrusion.

11. The wearable electronic device defined in claim 1 further comprising a glove-shaped wearable device housing structure coupled to the force sensor.

12. The wearable electronic device defined in claim 1 further comprising a wearable device housing, wherein the wearable device housing is configured to receive a body part, and wherein the force sensor is supported by the wearable device housing in a configuration in which the collapsible fluid-filled force sensor protrusion faces the body part, and wherein the force sensor is configured to make a physiological measurement on the body part.

13. The wearable electronic device defined in claim 1 further comprising an air pressure equalization opening in the force sensor structure.

14. The wearable electronic device defined in claim 1 wherein the force sensor structure comprises first and second layers of polymer that are coupled to each other to form the channel and wherein the first layer of polymer is configured to form the collapsible fluid-filled force sensor protrusion.

15. The wearable electronic device defined in claim 1 further comprising:
a printed circuit to which the pressure sensor is mounted; and
an attachment structure that is coupled to the printed circuit, wherein the attachment structure has a recessed surface and wherein the force sensor structure has a flexible polymer portion that is coupled to the attachment structure at the recessed surface.

16. The wearable electronic device defined in claim 15 further comprising sealant between the flexible polymer portion and the attachment structure at the recessed surface.

17. The wearable electronic device defined in claim 1 further comprising an electromagnetic actuator that is configured to pressurize the fluid and that is controlled by the control circuitry.

18. The wearable electronic device defined in claim 1 wherein the pressure sensor comprises a microelectromechanical systems pressure sensor.

19. A force sensor comprising:
a polymer structure forming a fluid-filled collapsible protrusion and a fluid-filled channel coupled to the fluid-filled collapsible protrusion, wherein the fluid-filled collapsible protrusion and fluid-filled channel are filled with a fluid, and wherein the fluid-filled collapsible protrusion has a first surface facing the fluid and a second surface facing away from the fluid; and
a pressure sensor coupled to the channel and configured to monitor pressure changes in the fluid to measure force on the second surface of the fluid-filled collapsible protrusion.

20. The force sensor defined in claim 19 wherein the fluid-filled collapsible protrusion comprises a collapsible fluid-filled dome.

21. A wearable electronic device, comprising:
a device housing configured to be worn on a body part of a user;
a polymer structure coupled to the device housing, wherein the polymer structure is configured to form a fluid-filled channel and a set of fluid-filled domes that are configured to contact the body part and that are coupled to the fluid-filled channel, wherein the fluid-filled domes and fluid-filled channel are filled with a fluid, and wherein the fluid-filled domes are configured to receive a force from the user;
a pressure sensor coupled to the channel and configured to monitor pressure changes in the fluid to measure the force on the fluid-filled domes; and
wireless communications circuitry configured to wirelessly transmit information on the measured force.

22. An electronic device configured to be used by a user, the electronic device comprising:
control circuitry; and
a force sensor that supplies a force sensor output signal to the control circuitry, wherein the force sensor comprises:
a collapsible fluid-filled force sensor protrusion having a cross-sectional shape that includes a circular arc, wherein the collapsible fluid-filled force sensor protrusion is configured to receive a force from the user;
a pressure sensor; and
a force sensor structure that is configured to form a channel, wherein the channel is filled with fluid and is coupled between the collapsible fluid-filled force sensor protrusion and the pressure sensor, wherein the pressure sensor is configured to generate the force sensor output signal in response to the force, and wherein the pressure sensor is configured to provide the force sensor output signal to the control circuitry.

23. The electronic device defined in claim 22 wherein the collapsible fluid-filled force sensor protrusion includes a portion forming a semi-circular channel.

24. The electronic device defined in claim 23 further comprising a wearable device housing that includes fabric and that is configured to be worn on a body part.

* * * * *